United States Patent

Bernhardi et al.

(10) Patent No.: US 6,681,639 B2
(45) Date of Patent: Jan. 27, 2004

(54) METHOD OF ESTIMATING THE LIFETIME OF THERMAL BARRIER COATINGS

(75) Inventors: Otto Bernhardi, Bad Schoenborn (DE); Roland Muecke, Windisch (CH); Hans Joachim Schmutzler, Maikammer (DE); Christoph Sommer, Meschede (DE); Marianne Sommer, Walldorf (DE)

(73) Assignee: Alstom (Switzerland) Ltd., Baden (CH)

( * ) Notice: Subject to any disclaimer, the term of this patent is extended or adjusted under 35 U.S.C. 154(b) by 10 days.

(21) Appl. No.: 10/120,416

(22) Filed: Apr. 12, 2002

(65) Prior Publication Data

US 2003/0037606 A1 Feb. 27, 2003

(30) Foreign Application Priority Data

Apr. 14, 2001 (DE) .......................................... 101 18 541

(51) Int. Cl.⁷ ................................................. G01N 3/32
(52) U.S. Cl. ................................................... 73/810
(58) Field of Search ........................ 73/762, 808, 811, 73/812, 813, 814, 815, 168

(56) References Cited

U.S. PATENT DOCUMENTS

| | | | | |
|---|---|---|---|---|
| 4,169,742 A | * | 10/1979 | Wukusick et al. | 148/404 |
| 4,388,124 A | * | 6/1983 | Henry | 148/404 |
| 4,643,782 A | * | 2/1987 | Harris et al. | 148/404 |
| 5,270,123 A | * | 12/1993 | Walston et al. | 428/652 |
| 5,366,695 A | * | 11/1994 | Erickson | 420/448 |
| 5,470,371 A | * | 11/1995 | Darolia | 75/229 |
| 5,540,790 A | * | 7/1996 | Erickson | 148/410 |
| 5,625,153 A | * | 4/1997 | Sawai et al. | 73/762 |
| 5,888,451 A | * | 3/1999 | Konter et al. | 420/448 |
| 6,007,645 A | * | 12/1999 | Cetel et al. | 148/404 |

FOREIGN PATENT DOCUMENTS

| EP | 0937786 A2 | 8/1999 |
|---|---|---|
| EP | 1031637 A1 | 8/2000 |

OTHER PUBLICATIONS

Robert A. Miller, "Oxidation–Based Model for Thermal Barrier Coating Life", Journal of the American Ceramic Society, vol. 67, No. 8, pp. 517–521, Aug. 1984.

* cited by examiner

*Primary Examiner*—Edward Lefkowitz
*Assistant Examiner*—Corey D. Mack
(74) *Attorney, Agent, or Firm*—Adam J. Cermak

(57) ABSTRACT

A method of estimating the lifetime of a thermal barrier coating (14), which is applied to the surface of a member subjected to cyclical thermal loads, especially a vane and/or blade of a gas turbine, by means of a bond coat (12) lying in between the coating and the member, leads to more accurate results with simplified calculation by determining, in a first step, the amplitude of the normal stress ($\Delta\sigma_n$) perpendicular to the interface between the bond coat (12) and the thermal barrier coating (14) during cyclical loading, and calculating, in a second step, the number $N_i$ of cycles to failure for every normal stress amplitude ($\Delta\sigma_n$) in accordance with the formula $$N_i = C\left(\frac{\Delta\sigma_n}{\sigma_0}\right)^m$$

where $\sigma_0$ is a stress reference value and $C(\delta_{ox})$ and $m(\delta_{ox})$ are material parameters, which depend on the thickness ($\Delta_{ox}$) of an oxide layer (13), which is located between the thermal barrier layer (14) and the bond coat (12) and grows with the cyclical loading.

8 Claims, 3 Drawing Sheets

METHOD OF ESTIMATING THE LIFETIME OF THERMAL BARRIER COATINGS

TECHNICAL FIELD

The present invention relates to the technical field of thermally highly stressed members, such as for example components (pistons or the like) of internal combustion engines, gas turbine blades, combustion chambers etc.

PRIOR ART

Thermally highly stressed components from the high-temperature region of gas turbines, such as for example blades or vanes, are coated for two reasons:
  to protect the blade or vane material from corrosive attacks, and
  to reduce the temperatures of the metal to a level, which can be withstood.

Usually, two coatings are applied to the base material. The first one is known as the "overlay" coating, which protects against corrosion. The second coating, which is usually referred to as the thermal barrier coating (TBC) and is only applied if need be, serves as the aforementioned thermal isolation.

However, components coated in such a way may also become defective for various reasons: mismatches with respect to the coefficients of thermal expansion between the various materials of which the member consists can cause thermal stresses and deformations in the system. Furthermore, instances of scaling due to oxidation and growth thereof at relatively high temperatures can produce additional stress loads.

These stresses and deformations can finally lead to cracking and spalling of the coating layers. According to FIG. 5, the coating system 10 is therefore usually made up of four different layers:
  the base material 11, which is usually several mm thick,
  the bond coat 12, which has a thickness of about 0.1 . . . 0.3 mm,
  a thermally grown oxide (TGO) layer 13, which grows to a thickness of 0.02 mm, and
  the thermal barrier coating 14, which is approximately 0.2 . . . 0.4 mm thick.

In-depth investigations of the stress/deformation behavior have already been carried out on the basis of finite-element networks, in which all four elements of the coating system were modeled in all details, including a nonlinear material behavior. It has been found in these investigations that both the thermal growth of the oxide layers and the creep behavior of the bond coats play a major part in the formation of defects (see in this respect, for example, the article by Freborg, A. M., Ferguson, B. L.: 'Modelling oxidation induced stresses in thermal barrier coatings'. Material Science and Engineering A245, 1998, pages 182–190). However, the results of these investigations cannot be used for predicting lifetimes.

SUMMARY OF THE INVENTION

It is therefore the object of the invention to specify a simplified method of estimating the lifetime of a thermal barrier coating, which also takes into account the part played by the changing oxide layer.

The object is achieved by the entirety of the features of claim 1. The essence of the invention is to use in the calculation of the number $N_i$ of cycles to failure material parameters $C(\delta_{ox})$ and $m(\delta_{ox})$ which depend on the thickness $(\delta_{ox})$ of an oxide layer, which is located between the thermal barrier coating 14 and the bond coat 12 and grows with cyclical loading.

The calculation is particularly simple here if, according to a preferred refinement of the method according to the invention, the dependence of the material parameters $C(\delta_{ox})$ and $m(\delta_{ox})$ on the thickness $(\delta_{ox})$ of the oxide layer is assumed to be linear, if furthermore a growth law of the form $$\delta_{ox} = k_p t^n$$

with a growth constant $k_p$ and an exponent n is used for the increase in the thickness $(\delta_{ox})$ of the oxide layer with time t, if a damage increment $\Delta D$, which satisfies the approximation formula $$\Delta D(N) \approx \frac{1}{C(N)}(\Delta \sigma_n)^{-m(N)}$$

is calculated, N giving the number of loading cycles, and $C(N)$ and $m(N)$ being parameters which satisfy the equations $$C(N) = \alpha_c (NT)^n + \beta_c$$

and $$m(N) = \alpha_m (NT)^n + \beta_m$$

with the exponent n, the constants $\alpha_c$, $\alpha_m$, $\beta_c$, $\beta_m$, and the holding time T at high temperature per loading cycle, and if the number of loading cycles to failure $N_i$ of the member is determined by the damage increment being summed up in accordance with the formula $$D = \sum_{N=1}^{N_i} \Delta D(N)$$

until D has reached the value 1.

Further embodiments are disclosed in the dependent claims.

BRIEF EXPLANATION OF THE FIGURES

The invention is to be explained in more detail below on the basis of exemplary embodiments in connection with the drawing, in which.

WAYS OF IMPLEMENTING THE INVENTION

Within the scope of the invention, the defect behavior caused by thermocyclic fatigue of the coating system is considered. This approach is justified in a certain way by the results obtained in experiments on vanes and blades in a fluidized bed, from which it becomes evident that a defect begins in the coating at the leading edge of the blade or vane airfoil and then spreads over the low-pressure side of the test piece as the number of loading cycles increases.

Possible fundamental variables which could be significant for the cyclical failure of the TBC layer are:

the region of mechanical deformation in the layer plane, the region of the stress perpendicular to the interface between the TBC layer and the bond coat (normal stress), the regions of stored mechanical energy.

It is assumed that the significant variable for the failure of the TBC layer is the region of mechanical stress, which is perpendicular to the interface between the TBC layer and the bond coat (normal stress $\sigma_n$). It is further presupposed that, if the coating system is loaded with normal stress cycles of constant stress amplitude ($\Delta\sigma$), and the oxide layer does not grow, the cyclical defect behavior of the TBC layer can be described in approximation by a standard defect equation of the Manson-Coffin type $$N_i = C\left(\frac{\Delta\sigma}{\sigma_0}\right)^m \qquad (1)$$

where $N_i$ is the number of cycles to failure (that is for example until spalling of the TBC layer at a critical point of the blade or vane surface), C and m are material constants which describe the defect behavior of the material, $\Delta\sigma$ is the region of normal stress, and $\sigma_0$ is a stress reference value It should be noted that the stress reference value $\sigma_0$ is introduced in order to make the expression in the parentheses of equation (1) dimensionless. The value of $\sigma_0$ is fixed, for example, at $$1\frac{N}{mm^2} = 10^{-6} \text{ Mpa}.$$

The aforementioned assumption corresponds to the assumption that the number of cycles to failure can be plotted as a straight line in a log ($\Delta\sigma$) against log ($N_i$) diagram, and that it depends on the upper temperature of the thermal cycles. In the actual implementation of the calculation method, this temperature dependence is taken into account by a suitable, piecewise linear interpolation.

Figure 1:
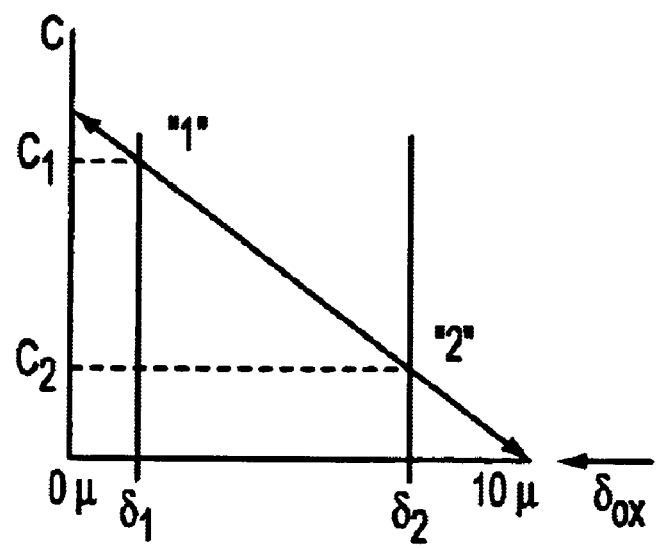
FIG. 1 shows the simplified, linear dependence of the defect constant C on the thickness $\delta_{ox}$ of the oxide layer assumed for the determination of the lifetime.

There is also experimental evidence to suggest that the cyclical defect resistance of the TBC layer depends on the thickness of the oxide layer $\delta_{ox}$ at the beginning, when no oxide layer has formed as yet, there is the greatest defect resistance. However, after the oxide layer has grown to a critical thickness (of typically 10 ... 14 $\mu$m), the TBC layer spalls, even if there is no significant cyclical loading. To simulate this defect behavior, it is assumed that the lifetime parameters C and m—in addition to the dependence on temperature—decrease linearly with increasing thickness $\delta_{ox}$ of the oxide layer, as represented in FIG. 1 by way of example for the parameter C. A further assumption is required for the growth of the thickness $\delta_{ox}$ of the oxide layer with time. For this, the following, well-known growth law is used:

$$\delta_{ox} = k_p t^n. \qquad (2)$$

The growth of the oxide layer is accordingly described by a growth constant $k_p$ and an exponent n. The exponent n typically has a value of 0.5; i.e., the growth over time of the oxide layer is assumed to be proportional to the root of the time. However, the value n can in principle also assume other values. Furthermore, it is known of the growth constant $k_p$ that it increases with temperature. It is therefore introduced as a temperature-dependent variable.

The defect behavior of the TBC layer is simulated by the defect constants C and m being assigned a dependence on the oxide layer thickness according to FIG. 1. The defect constant C, for example, decreases with increasing oxide layer thickness $\delta_{ox}$ linearly to zero. The linear behavior can be completely fixed by prescribing two points "1" and "2" (FIG. 1), to which the corresponding error constants $C_1$ and $C_2$ and also $\delta_1$ and $\delta_2$ are assigned. The defect constant C is in this way a function of the oxide layer thickness according to:

$$C(\delta_{ox}) = C_1 + \frac{C_2 - C_1}{\delta_2 - \delta_1}(\delta_{ox} - \delta_1) \qquad (3)$$

A corresponding relationship is obtained for the defect exponent m:

$$m(\delta_{ox}) = m_1 + \frac{m_2 - m_1}{\delta_2 - \delta_1}(\delta_{ox} - \delta_1) \qquad (4)$$

If the growth law from equation (2) is then introduced, the following is obtained for equation (3):

$$C(t) = C_1 + \frac{C_2 - C_1}{\delta_2 - \delta_1}(k_p t^n - \delta_1). \qquad (5)$$

A corresponding relationship, which is not given here for the sake of simplicity, is obtained for the defect exponent m. The equation (5) can be written as $$C(t) = \alpha_c t^n + \beta_c \qquad (6)$$

with the following abbreviations:

$$\alpha_c = \frac{C_2 - C_1}{\delta_2 - \delta_1} k_p \qquad (7)$$

and $$\beta_c = C_1 + \frac{C_2 - C_1}{\delta_2 - \delta_1}\delta_1 \qquad (8)$$

The time t is represented in approximation by the product from the respective number N of loading cycles and the holding time T (at high temperature), the holding time being assumed to be long in comparison with the transitional times between the cycles:

$$t = NT \qquad (9)$$

Following from this for (6) is:

$$C(N) = \alpha_c (NT)^n + \beta_c \qquad (10)$$

and, correspondingly, for the exponent m:

$$m(N) = \alpha_m (NT)^n + \beta_m \qquad (11)$$

Corresponding then to the defect equation or damage equation (1) is the following equation for the damage rate dD as a function of the rate dN of the loading cycles:

$$dD = \frac{1}{C(N)}(\Delta\sigma_n)^{-m(N)}dN = \frac{1}{\alpha_c(NT)^n + \beta_c}(\Delta\sigma_n)^{-(m_1 + \alpha_m(NT)^n + \beta_m)}dN. \quad (12)$$

A defect occurs if the following conditions apply:

$$D=1 \text{ and } N=N_i \quad (13)$$

Since the equation (12) cannot be analytically integrated, a simple summation is used. For this purpose, the following approximation is made:

$$\Delta D \approx dD = \frac{1}{C(N)}(\Delta\sigma_n)^{-m(N)} \quad (14)$$

and summed up:

$$D = \sum_{N=1}^{N_1} \Delta D. \quad (15)$$

Since $N_i$ is not known, the summation is continued until one of the two conditions is satisfied:

$$D \geq 1 \text{ or } \Delta D \leq 0. \quad (16)$$

As already mentioned, that mechanical variable which is relevant for the lifetime of the TBC layer is the stress perpendicular to the interface between the TBC layer and the adjacent bond coat. However, this normal stress cannot be taken from the currently used finite element models, because the base material is normally modeled by finite volume elements. The relatively weak mechanical behavior of the thin top coats is ignored in this.

The thickness of the TBC layer is small in comparison with the thickness of the neighboring metal wall. Furthermore, the elastic rigidity of the TBC layer is typically very much less (usually by an order of magnitude) than the rigidity of the metal. This permits the assumption that the total stress which acts in the TBC layer tangentially to the surface of the member is determined by the total tangential stress of the base material.

Figure 2:
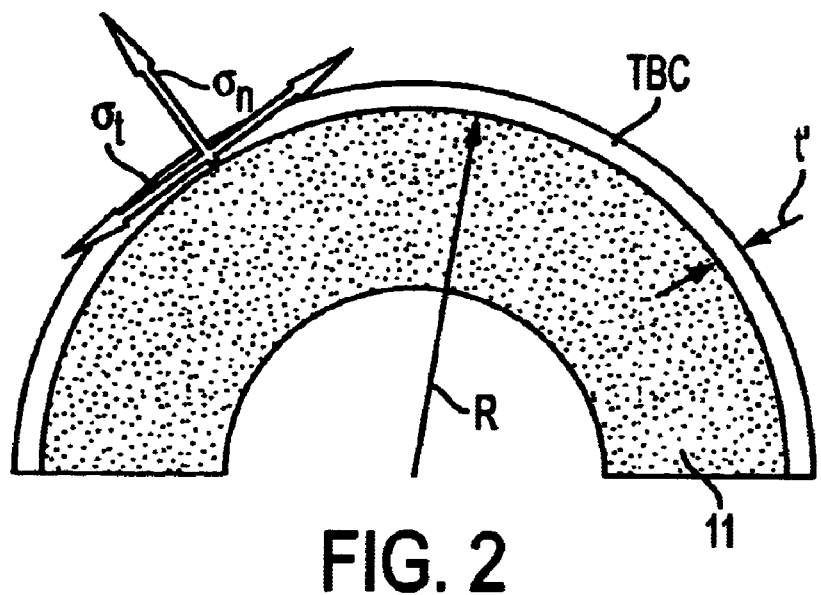
FIG. 2 shows the stress components (normal stress and tangential stress) in the case of a cylindrical test piece.

Furthermore, the stress acting perpendicular to the interface between the TBC layer and the bond coat (normal stress) $\sigma_n$, can then be estimated if the size of the surface curvature is known. In the case of a cylindrical member, this estimate corresponds to the known "cylinder formula"

$$\sigma_n = \frac{t'}{R}\sigma_t \quad (17)$$

where $\sigma_n$ represents the normal stress and $\sigma_t$ represents the tangential stress in the TBC layer and t' and R denote the thickness of the TBC layer and the radius of curvature (see FIG. 2).

The method actually used for determining the normal stress is a little more complicated for the following reasons:

- In most cases, there is a two-dimensional tangential stress.
- The members for consideration generally have doubly (convexly, concavely) curved surfaces.
- The determination of the curvature parameters should be applicable to volume element networks with different types of volume elements, including linear elements, the surface of which does not have any independent curvature at all.

For the estimate of the normal stress, a method which reverts to formulations of the standard shell theory, which are not to be explained in any more detail here, is therefore used.

The experience acquired so far on the deformation behavior of the TBC layers suggests the presumption that the stresses in the TBC layer decrease at high temperatures and therefore disappear during the holding times at high temperatures (i.e. if the member is operated at full load). After cooling to room temperature, perpendicular tensile stresses develop at the interface between the TBC layer and the bond coat, because, in the case of the members (components) concerned, the thermal coefficients of expansion for the TBC layer are less than for the base material.

It can therefore be assumed that, at room temperature, the coating system is subjected to perpendicular tensile stress. At high temperatures, the coating does not undergo any mechanical loading, but the materials are exposed to corrosive attacks and associated degradation processes. A nonlinear finite element analysis for multiple cycles, which also takes into account creep effects can predict the correct cycle properties here.

If, however, a linear finite element analysis is used as a basis for the estimation of the lifetime of the TBC layer, a loading cycle with reversed characteristics is calculated: no stresses (including the perpendicular stresses) at room temperature and maximum perpendicular (compressive) stresses at operating temperature.

To overcome these differences and keep the method of determination simple, the absolute values of the regions of the normal stress are used for the determination. However, this approximation neglects possible differences in lifetime for TBC layers with convex and concave curvature, because the corresponding difference in the algebraic signs of the perpendicular stresses is ignored.

The damage coefficient C and the exponent m are fixed by prescribing the values of $C_1(T_i)$ and $C_2(T_i)$ for a suitable set of different temperatures $T_i$. Furthermore, the corresponding thickness values $\delta_1(T_i)$ and $\delta_2(T_i)$ must be defined.

$C_1(T_i)$ will consequently usually be the temperature-dependent defect coefficient for the "virginal" TBC system, which has not yet oxidized. In a corresponding way, $\delta_2(T_i)$ is usually the oxide layer thickness, which immediately makes the TBC layer defective without it being subjected to any appreciable fatigue loading.

To be able to define the parameters of the oxidation rate, values for the exponent $m(T_i)$ and the coefficient $k_p(T_i)$ of the oxidation rate are required. Finally, the holding time of the loading cycles considered is also required.

So far, only relatively few experimental data exist for the determination of the aforementioned parameters of the model used. However, a series of thermal shock experiments have already been carried out in a fluidized bed setup, a set of preoxidized blade portions being used to investigate the spalling behavior of the TBC layers.

After the preoxidation at three different temperatures, the test pieces were exposed to alternating thermal loading in the fluidized bed installation. The holding time at the upper temperature was 5 minutes. The total loading time during the alternating loading in the fluidized bed was therefore small in comparison with the duration of the preoxidation. The test results can therefore be used for the rough estimate of the required defect parameters, on the assumption that no change in the defect parameters C and m takes place during the alternating loading. However, it must be noted that, during the operation of an actual machine (gas turbine etc.), the holding times are to be measured in hours or even in days, and that usually no preoxidation takes place there. Therefore, for example in the case of a gas turbine blade in use, the defect parameters will most probably change considerably during the lifetime of the component.

Figure 3:
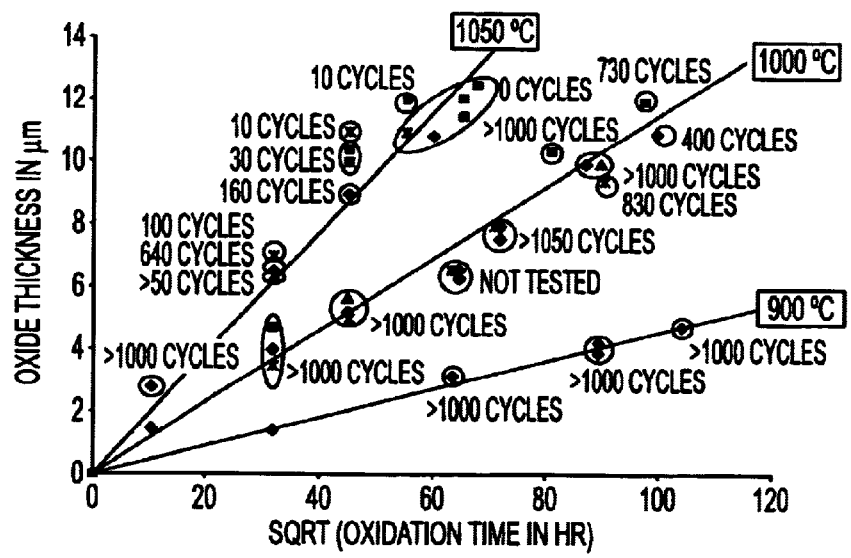
FIG. 3 shows experimental results for the lifetime and the thickness of the oxide layer in dependence on the preoxidation period.

Some important results of these experimental investigations are reproduced in FIG. 3, where the thickness of the oxide layer is plotted against the root of the preoxidation period. In addition, the measured numbers of load cycles to failure of the TBC layer are entered in the figure. For many of the experiments, the alternating loading was discontinued after 1000 cycles, so that only a few data points can be used for the estimate of the defect parameters.

The spalling of the TBC layers usually begins at the leading edge of the test pieces, where the normal stress is greatest. In a corresponding way, the numbers of load cycles, which led to a first defect in the TBC layer (at the leading edge) are entered in FIG. 3. For all the test pieces except one, however, no further load cycles were carried out to measure the progression of the layer detachment in the less strongly curved regions of the test pieces.

The following results can be summarized from FIG. 3 and the investigation of the test pieces:

- In the plotting of FIG. 3, the oxide layer thickness is approximated by straight lines, the slopes of which increase with the temperature. This suggests that the thickness of the oxide layer is approximately proportional to the root of the oxidation period. Therefore, the exponent n=0.5 is used for the equation (2). Furthermore, the temperature-dependent values for the coefficient $k_p$ can be read off from the diagram.
- The cyclical properties of the defects in the TBC layer are confirmed by FIG. 3; the dependence of the numbers of load cycles on the thickness of the oxide layer is obvious.
- The number of load cycles until there is a defect at the front edge (leading edge) of the blade tends toward zero if the thickness of the oxide layer reaches a limit value of 12 ... 14 µm. It has additionally been observed that the defective region becomes larger and spreads from the front edge into less strongly curved regions when the thickness of the oxide layer approaches this limit value. This shows that, with increasing oxide layer thickness, the defect properties become more and more independent of the normal stress as soon as the oxide layer thickness approaches the limit value 12 ... 14 µm.
- Test pieces which have been preoxidized sufficiently long, so that their oxide layer thickness reached the limit value 12 ... 14 µm, tend to exhibit spalling over the entire test piece without any further load cycles; the TBC layer simply falls from the test piece as soon as it is removed from the preoxidation oven and is cooled to room temperature.
- The defect exponent characterizes the dependence of the number of cycles to failure on the normal stress: an exponent of m=0 means there is no dependence of the failure on the normal stress. In the case of the aforementioned experiments, this is obviously the case for strongly preoxidized test pieces, on which the TBC layer spalls from virtually all the surface regions irrespective of the curvature. It is therefore to be expected that the exponent tends toward zero when the thickness of the oxide layer approaches its "limit value".

To determine the value of the defect exponent m, one of the blade portions was subjected to continual cyclical loading after the occurrence of the first defect at the blade tip, while the progression of the spalled region to less strongly curved regions was recorded. For this experiment, a "Coated" coating with a thickness of 0.6 mm was used. The duration of the preoxidation was 10,000 h at 1000° C. By analogy with the other experiments, a holding time of 5 minutes was used at the upper cycle temperature during the alternating loading in the fluidized bed installation. Therefore, the total period at the upper temperature is small in comparison with the preoxidation period, as long as the number of cycles is less than about 1000. It can therefore be assumed that the thickness of the oxide layer is constant throughout the alternating loading.

As expected, the defect spread into the low-pressure side. On the high-pressure side, no defect was observed. The results obtained In this way are listed in the following table 1:

TABLE 1

| Progression of the defect region [mm] | Curvature in the defect region [mm] | Normal stress [Nmm$^{-2}$] | Number of cycles to failure |
|---|---|---|---|
| 0.0 | 6.2 | 11.6 | 730 |
| 50.2 | 28.9 | 2.49 | 860 |
| 51.8 | 45.1 | 1.6 | 1600 |
| 62.8 | 112.0 | 0.643 | 1700 |
| 66.0 | 171.0 | 0.42 | 1970 |

The tangential stress (thermal mismatch) $\sigma_t$ was estimated under the following assumptions:

thermal coefficient of expansion of the base material: $\alpha_{base}=16\cdot 10^{-6}$ thermal coefficient of expansion of the TBC layer: $\alpha_{TBC}=10\cdot 10^{-6}$ modulus of elasticity of the TBC layer: $E_{TBC}=20,000$ Nmm$^{-2}$ thickness of the TBC layer: 0.6 mm Furthermore, the following relationship was used:

$$\sigma_t = E_{TBC}(\alpha_{base}-\alpha_{TBC})\Delta T. \tag{18}$$

The values for the normal stress $\sigma_n$ were calculated by means of the equation (17).

Figure 4:
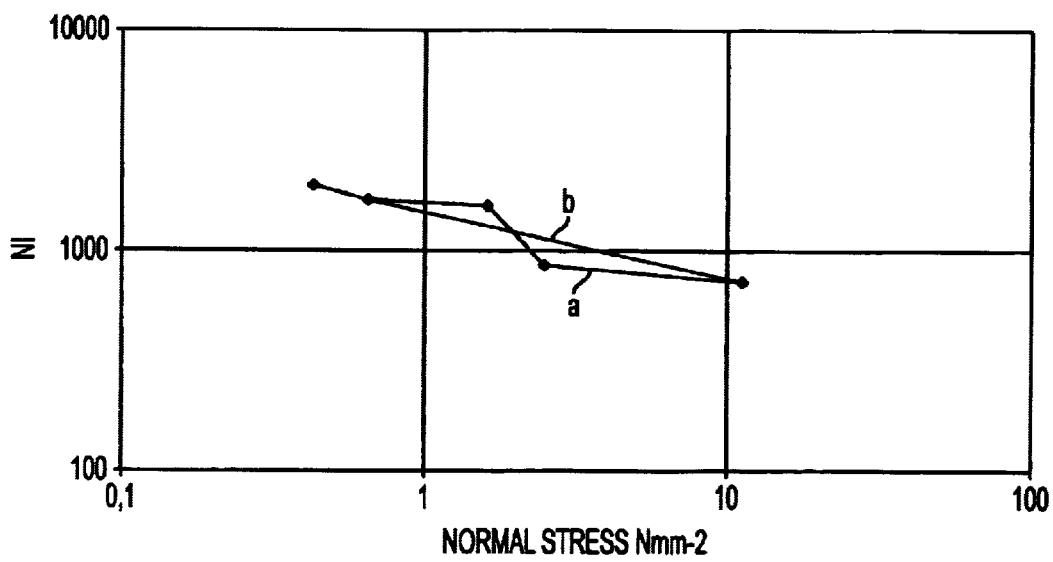
FIG. 4 shows the measured dependence (curve a) and the calculated dependence (curve b) of the number of cycles to failure of the normal stress for a test piece with a 0.6 mm Coated thermal barrier coating.
Figure 5:
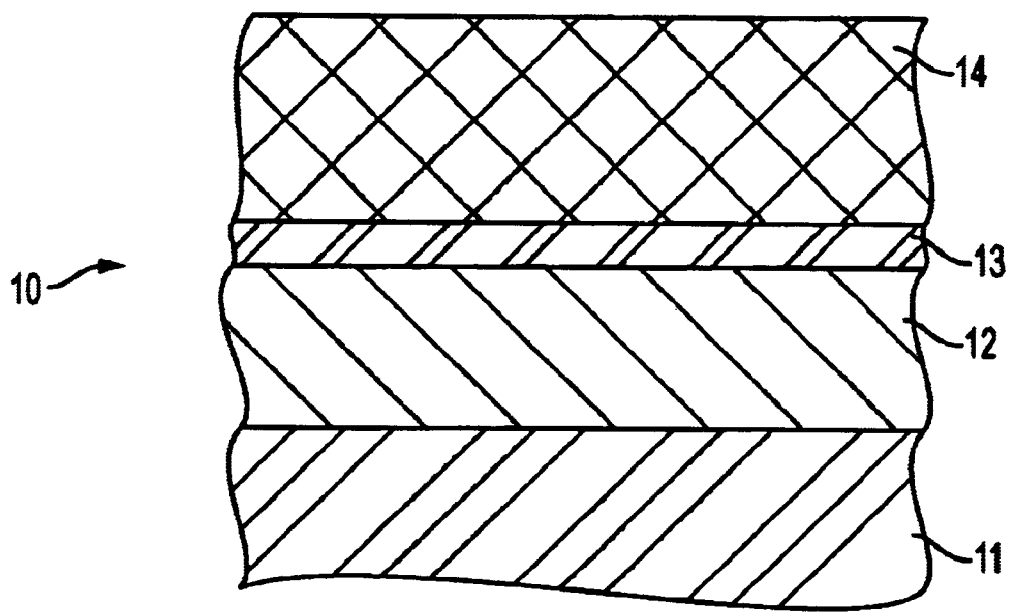
FIG. 5 shows the schematic structure of a coating system with a thermal barrier coating.

The resulting numbers of cycles to failure were plotted against the normal stress, as represented in FIG. 4 (curve a). An approximation with the defect parameters m=−0.3 and C=1500 is likewise depicted in FIG. 4 (curve b). These parameters are valid for 1000° C. upper cycle temperature and for alternating loading with an oxide layer with a constant thickness near the "limit value" of 12 ... 14 µm. For the case of thinner oxide layers (i.e. with a shorter preoxidation period), the parameter m will probably assume higher values, perhaps of the order of magnitude of −2 ... −5, similar to the m defect parameters of the base material.

For the determination of the defect coefficient C, the same assumptions are made as above, i.e. the thickness of the oxide layer is assumed to be constant during the alternating loading in the fluidized bed installation.

For a first rough estimation, it is presupposed that the same defect exponent m=−0.3 is valid. The defect coefficients C can then be calculated simply according to the equation $$C = \left(\frac{\Delta\sigma}{\sigma_0}\right)^{-m} N_i \tag{19}$$

where the normal stress $\Delta\sigma_n$ at the leading or front edge (highest value)=11.6 Nmm$^{-2}$ and $\sigma_0$=1.0 Nmm$^{-2}$.

The values obtained in this way for C are listed in the following table 2.

TABLE 2

| Temperature [° C.] | Thickness of the TBC layer [mm] | Normal stress [Nmm$^{-2}$] | Thickness of oxide layer [μm] | Cycles | C |
|---|---|---|---|---|---|
| 1050 | 0.3 | 5.6 | 6.5 | 640 | 380 |
| 1050 | 0.3 | 5.6 | 9 | 160 | 95 |
| 1000 | 0.3 | 5.6 | 10.8 | 400 | 240 |
| 1000 | 0.3 | 11.1 | 12 | 730 | 350 |

The two rows in table 2 for T=1050° C. permit an estimation of C as a function of the oxide layer thickness, that is for example the definition of values $C(\delta_{ox})$. Unfortunately, this is not possible for the temperature 900° C., because no $N_i$ data are available for this. Furthermore, the observed rising C value for the temperature of 1000° C. must be ascribed to a variance in the measured lifetime data.

For the described calculation method, a computer program with the designation COAT has been created, comprising a source code in the language C and using among the input data values which have been calculated in advance by means of the known finite element program ABAQUS.

Apart from various subprograms within the COAT software, there are FORTRAN routines which serve as an interface with respect to the .fil file of ABAQUS. Access to the HKS-ABAQUS libraries is not necessary. The COAT program can therefore run independently of ABAQUS. It is assumed here that the entire data of the mechanical deformation, thermal expansion and temperature are stored in the .fil result file of ABAQUS. Corresponding specifications for this must be prescribed within the EL FILE definitions of the ABAQUS inputs. The resulting data for the elements must be stored using the keyword *EL FILE, POSITION=AVERAGED AT NODES.

LIST OF REFERENCE NUMERALS

| | |
|---|---|
| 10 | coating system |
| 11 | base material |
| 12 | bond coat |
| 13 | oxide layer |
| 14 | thermal barrier coating (TBC) |
| a, b | curve |
| C, C$_1$, C$_2$ | defect constant |
| δ$_{OX}$, δ$_1$, δ$_2$ | thickness of oxide layer |
| R | radius of curvature |
| t' | thickness of thermal barrier coating |
| σ$_n$ | normal stress |
| σ$_t$ | tangential stress |

What is claimed is:

1. A method of estimating the lifetime of a thermal barrier coating, which is applied to the surface of a member subjected to cyclical thermal loads, especially a vane and/or blade of a gas turbine, by a bond coat lying in between the coating and the member, the method comprising:

in a first step, determining the amplitude of the normal stress ($\Delta\sigma_n$) perpendicular to the interface between the bond coat and the thermal barrier coating during cyclical loading; and, in a second step, calculating the number $N_i$ of cycles to failure for every normal stress amplitude ($\Delta\sigma_n$) in accordance with the formula $$N_i = C\left(\frac{\Delta\sigma_n}{\sigma_0}\right)^m$$

where $\sigma_0$ is a stress reference value and $C(\delta_{ox})$ and $m(\delta_{ox})$ are material parameters, which depend on the thickness ($\delta_{ox}$) of an oxide layer, which is located between the thermal barrier layer and the bond coat and grows with the cyclical loading.

2. The method as claimed in claim 1, comprising: assuming the dependence of the material parameters $C(\delta_{ox})$ and $m(\delta_{ox})$ on the thickness ($\delta_{ox}$) of the oxide layer to be linear.

3. The method as claimed in claim 2, comprising: using a growth law of the form $$\delta_{ox}=k_p t^n$$

with a growth constant $k_p$ and an exponent n for the increase in the thickness ($\delta_{ox}$) of the oxide layer with time t, calculating a damage increment $\Delta D$, which satisfies the approximation formula $$\Delta D(N) \approx \frac{1}{C(N)}(\Delta\sigma_n)^{-m(N)}$$

N giving the number of loading cycles, and C(N) and m(N) being parameters, which satisfy the equations $$C(N)=\alpha_c(NT)^n+\beta_c$$

and $$m(N)=\alpha_m(NT)^n+\beta_m$$

with the exponent n, the constants $\alpha_c$, $\alpha_m$, $\beta_c$, $\beta_m$, and the holding time T at high temperature per loading cycle, and determining the number of loading cycles to failure $N_i$ of the member by the damage increment being summed up in accordance with the formula $$D = \sum_{N=1}^{Ni} \Delta D(N)$$

until D has reached the value 1.

4. The method as claimed in claim 3, comprising: using an exponent n of approximately 0.5 in the growth law.

5. The method as claimed in claim 4, comprising: determining the normal stress amplitude ($\Delta\sigma_n$) on the surface of the member by a finite element method.

6. The method as claimed in claim 3, comprising: determining the normal stress amplitude ($\Delta\sigma_n$) on the surface of the member by a finite element method.

7. The method as claimed in claim 2, comprising: determining the normal stress amplitude ($\Delta\sigma_n$) on the surface of the member by a finite element method.

8. The method as claimed in claim 1, comprising: determining the normal stress amplitude ($\Delta\sigma_n$) on the surface of the member by a finite element method.

* * * * *